US012636186B2

(12) United States Patent
Govari

(10) Patent No.: US 12,636,186 B2
(45) Date of Patent: May 26, 2026

(54) SYSTEM AND METHOD FOR DETECTION OF CORNEA COLLAPSE

(71) Applicant: JOHNSON & JOHNSON SURGICAL VISION, INC., Irvine, CA (US)

(72) Inventor: Assaf Govari, Haifa (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 69 days.

(21) Appl. No.: 18/409,293

(22) Filed: Jan. 10, 2024

(65) Prior Publication Data

US 2025/0221851 A1      Jul. 10, 2025

(51) Int. Cl.
*A61F 9/007* (2006.01)
*A61B 17/00* (2006.01)

(52) U.S. Cl.
CPC ... *A61F 9/00736* (2013.01); *A61B 2017/00057* (2013.01); *A61B 2217/005* (2013.01); *A61B 2217/007* (2013.01)

(58) Field of Classification Search
CPC ............. A61F 9/00736; A61F 9/00745; A61B 2017/00057; A61B 2217/005; A61B 2217/007
See application file for complete search history.

(56) References Cited

U.S. PATENT DOCUMENTS

| | | | |
|---|---|---|---|
| 4,902,122 A | 2/1990 | Azema et al. | |
| 6,613,041 B1 | 9/2003 | Schrunder | |
| 8,622,951 B2 | 1/2014 | Claus | |
| 10,307,051 B2 | 6/2019 | Ootsuki | |
| 10,456,030 B2 | 10/2019 | Buckland et al. | |
| 10,765,558 B2 | 9/2020 | Haeggstrom et al. | |
| 2009/0306581 A1* | 12/2009 | Claus | A61B 90/20 604/22 |
| 2022/0192876 A1* | 6/2022 | Algawi | A61F 9/00745 |

FOREIGN PATENT DOCUMENTS

| | | |
|---|---|---|
| EP | 3113669 B1 | 1/2017 |
| KR | 374672 Y1 | 2/2005 |
| WO | 2021033211 A1 | 2/2021 |
| WO | 2023170498 A1 | 9/2023 |
| WO | 2023209550 A1 | 11/2023 |

* cited by examiner

*Primary Examiner* — Brooke Labranche

(57) ABSTRACT

A system and method for use in eye surgery. The system includes at least one light source, a detection unit, and a detection circuit. The at least one light source is configured and operable to emit one or more illumination beams directed at a region of a corneal surface of a patient's eye. The detection unit includes an arrangement of light detectors positioned for collecting a reflected beam reflected from the region of the corneal surface of the patient's eye. The detection circuit is configured for collecting and analyzing a detection signal from the detection unit, and for detecting variations of the reflected beam pattern over time indicative of surface curvature changes of the corneal surface region. In response to detecting surface curvature change exceeding a predefined threshold, the detection circuit generate a response signal triggering operation of an anti-vacuum surge (AVS) mechanism.

10 Claims, 2 Drawing Sheets

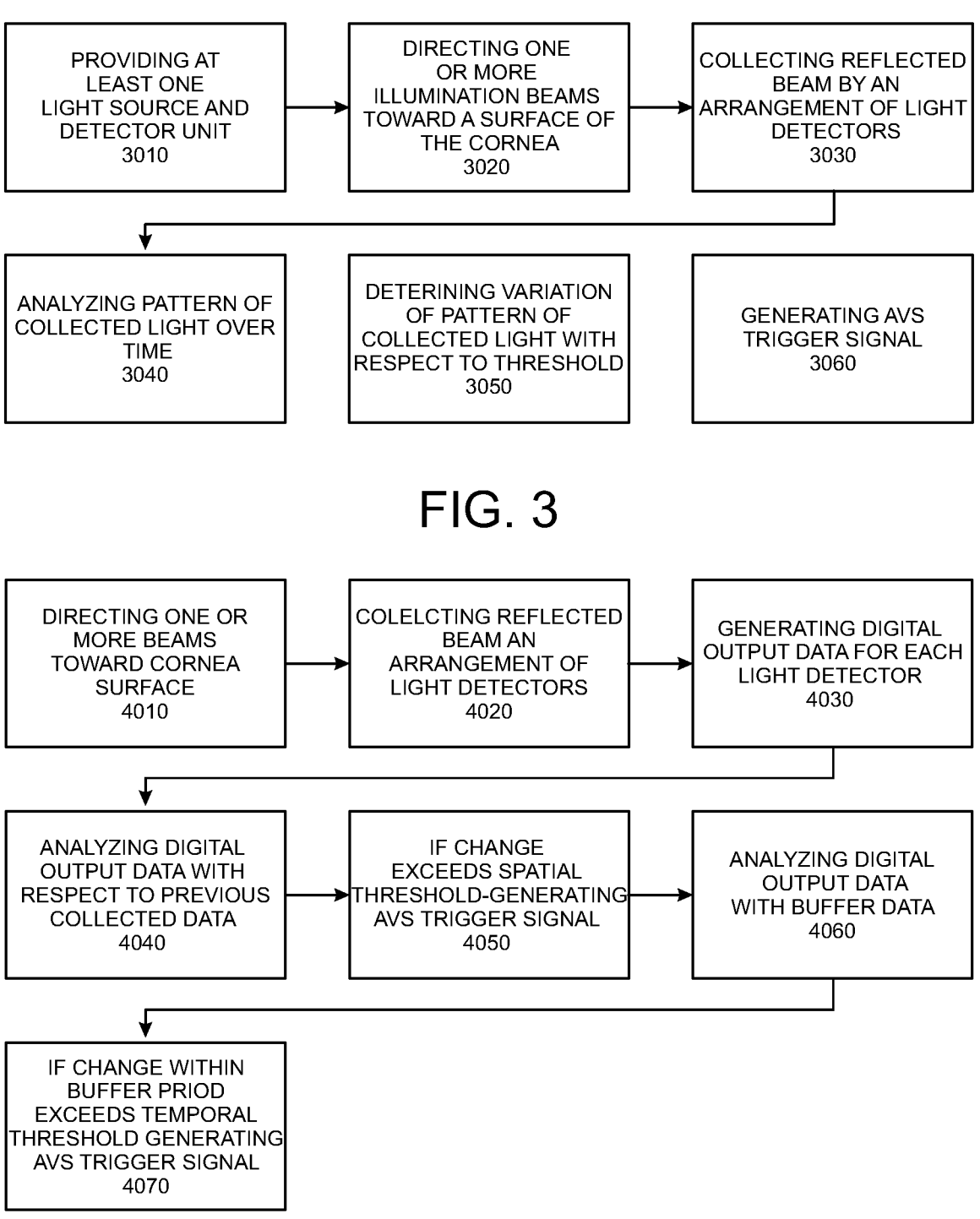

PROVIDING AT
LEAST ONE
LIGHT SOURCE AND
DETECTOR UNIT
3010

DIRECTING ONE
OR MORE
ILLUMINATION BEAMS
TOWARD A SURFACE OF
THE CORNEA
3020

COLLECTING REFLECTED
BEAM BY AN
ARRANGEMENT OF LIGHT
DETECTORS
3030

ANALYZING PATTERN OF
COLLECTED LIGHT OVER
TIME
3040

DETERINING VARIATION
OF PATTERN OF
COLLECTED LIGHT WITH
RESPECT TO THRESHOLD
3050

GENERATING AVS
TRIGGER SIGNAL
3060

FIG. 3

DIRECTING ONE OR
MORE BEAMS
TOWARD CORNEA
SURFACE
4010

COLELCTING REFLECTED
BEAM AN
ARRANGEMENT OF
LIGHT DETECTORS
4020

GENERATING DIGITAL
OUTPUT DATA FOR EACH
LIGHT DETECTOR
4030

ANALYZING DIGITAL
OUTPUT DATA WITH
RESPECT TO PREVIOUS
COLLECTED DATA
4040

IF CHANGE
EXCEEDS SPATIAL
THRESHOLD-GENERATING
AVS TRIGGER SIGNAL
4050

ANALYZING DIGITAL
OUTPUT DATA
WITH BUFFER DATA
4060

IF CHANGE WITHIN
BUFFER PRIOD
EXCEEDS TEMPORAL
THRESHOLD GENERATING
AVS TRIGGER SIGNAL
4070

FIG. 4

SYSTEM AND METHOD FOR DETECTION OF CORNEA COLLAPSE

TECHNOLOGICAL FIELD

The presently disclosed subject matter generally relates to the field of eye surgery, and more particularly relates to detection of variation in cornea curvature and prevention of cornea collapse during surgery.

BACKGROUND

Phacoemulsification is a surgical procedure used to treat cataracts, which is associated with clouding of the eye's lens and can cause blurred vision, difficulty seeing at night, and sensitivity to light. during the procedure, a surgeon makes small incision in the patient's cornea and inserts a probe to emit ultrasonic waves breaking the cataract tissue to small pieces. The pieces of the tissue can be suctioned out of the eye, where an artificial lens can be placed.

During the cataract surgery, the surgical site is irrigated to maintain a defined pressure level within the cornea chamber. This is to maintain cornea structure and prevent permanent damage to the patient's eye.

GENERAL DESCRIPTION

Irrigation of the surgical site during cataract surgery may include applying vacuum conditions for aspirating emulsified lens material from the capsular bag. If a vacuum surge occurs, the cornea may collapse and may lead to irreversible damage to the eye.

Typical phacoemulsification systems have some type of way to minimize post occlusion surge. For example, an anti-vacuum surge (AVS) mechanisms or device configured to stop vacuum operation to prevent eye damage. The present disclosure utilizes an optical arrangement for real-time detection of cornea curvature changes caused by post occlusion surge to activate an AVS mechanism when needed to prevent damage to the patient's eye.

To this end the present disclosure provides an optical arrangement for tracking cornea curvature, detecting variations in the cornea curvature, and operating the AVS mechanism if variation in cornea curvature exceeds at least one of spatial and temporal thresholds. The optical arrangement comprises at least one light source (e.g., laser light source) positioned and configured for directing one or more illumination beams of a selected wavelength range, to impinge on the patient's cornea at a selected angle, and a detection unit position for detecting reflected illumination, reflects from the surface of the cornea. The detector unit may comprise a selected arrangement of photodetectors (e.g., photodiodes) for identifying variation in location and/or spatial distribution of the reflected illumination beam.

The detector unit may be connected to an analog to digital conversion circuit (ADC). The ADC may be configured for converting detection data and generating digital output data indicative of at least one of spatial location and distribution of illumination beam reflected from the cornea and impinging on the detector unit.

The ADC is further connected to a decision circuit and/or processor, configured to determine variation in at least one of spatial location and distribution of illumination beam impinging on the detector, and if the variation exceeds at least one of spatial and/or temporal thresholds, the decision circuit is operable for triggering the AVS mechanism.

Accordingly, variation in cornea curvature, being a surface from which the illumination beam is reflected, affects at least one of location and distribution of illumination beam impinging on the detector unit. If such variation is detected the decision circuit may operate the AVS mechanism to stop vacuum operation to thereby maintain pressure within the eye region and thus eliminate, or at least significantly reduce risk to the patient's eye. Further, the ADCs and decision circuits may be configured as high-speed circuits providing for operation of the AVS within a time frame of 1-3 milliseconds or less.

The high-speed response may be achieved using a plurality of parallel operated ADCs, each connected to a respective detector of the detector unit and decision circuit operable for determining variation in detected signal with respect to predetermined spatial and/or temporal thresholds. In this connection, the spatial threshold relates to variation in location and/or distribution of the illumination beam, typically associated with magnitude of curvature change of the cornea. This is while the temporal threshold relates to rate of change of the location and/or distribution of the illumination beam, being associated with rate of variation of cornea curvature.

BRIEF DESCRIPTION OF THE DRAWINGS

In order to better understand the subject matter that is disclosed herein and to exemplify how it may be carried out in practice, examples will now be described, by way of non-limiting example only, with reference to the accompanying drawings, in which:

FIG. 3 illustrates a method for monitoring corneal curvature according to some examples of the present disclosure; and FIG. 4 illustrates an additional method for monitoring corneal curvature according to some examples of the present disclosure.

DETAILED DESCRIPTION OF EMBODIMENTS

In the following detailed description, numerous specific details are set forth in order to provide a thorough understanding. However, it will be understood by those skilled in the art that the presently disclosed subject matter may be practiced without these specific details. In other instances, well-known methods and features have not been described in detail so as not to obscure the presently disclosed subject matter.

Unless specifically stated otherwise, as apparent from the following discussions, it is appreciated that throughout the specification discussions utilizing terms such as "processing", "computing", "comparing", or the like, refer to the action(s) and/or process(es) of a computer that manipulate and/or transform data into other data, said data represented as physical, such as electronic, quantities and/or said data representing the physical objects. The term "computer" should be expansively construed to cover any kind of hardware-based electronic device with data processing capabilities.

The various illustrative logical blocks, modules, and algorithm steps described in connection with the examples disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing any departure from the scope of the disclosure.

It will also be understood that a system according to the present disclosure may be, at least partly, implemented on a suitably programmed computer. Likewise, the present disclosure contemplates a computer program being readable by a computer for executing the method of the present disclosure. The present disclosure further contemplates a non-transitory computer-readable memory tangibly embodying a program of instructions executable by the computer for executing the method of the present disclosure.

Figure 1:
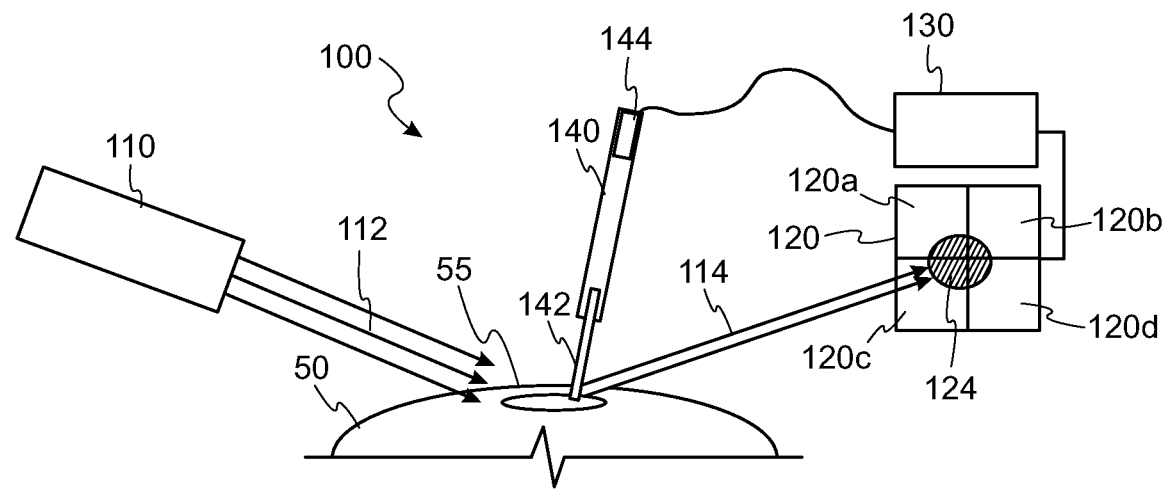
FIG. 1 illustrates a system for monitoring corneas surface curvature according to some examples of the present disclosure.

As indicated above, the present disclosure provides a system and method for use in eye surgery operations. FIG. 1 exemplifies a system 100 usable for monitoring corneal surface curvature during surgical operation of the eye. System 100 includes at least one light source 110, a detection unit 120, and a detection circuit 130. System 100 may be coupled with a phacoemulsification system, exemplified in FIG. 1 by handpiece 140. In this connection, a phacoemulsification system includes several elements such as irrigation and aspiration modules, controller including one or more processors, etc. The phacoemulsification system is exemplified in FIG. 1 by handpiece 140 including a distal end 142 that includes at least a needle and a sleeve and configured for applying vibration to emulsify lens tissue of the patient's eye and provide irrigation fluid and aspiration pumping as part of the surgical operation. Additionally, the phacoemulsification system includes an anti-vacuum surge (AVS) mechanism 144. AVS mechanism 144 is configured to end pumping operation of the aspiration module to eliminate vacuum pressure condition within the patient's eye to thereby avoid collapse of the cornea 50 due to low pressure conditions. For example, AVS mechanism 144 may include one or more valves located in path of aspiration line or aspiration channel and configured to close the aspiration channel to prevent post occlusion vacuum surge. In some other examples, the phacoemulsification system may utilize alternative configurations utilizing one or more valves for blocking aspiration channel. In some further additional examples, the phacoemulsification system may utilize electrical circuit connected to one or more pumps operating aspiration action of the phacoemulsification system, to selectively vary pump operation and/or shut off the pump operation. AVS mechanism 144 is exemplified in FIG. 1 as being placed within the handpiece 140 of the phacoemulsification system. It should be understood that AVS mechanism 144 may be located in various other locations within the system and/or externally to the phacoemulsification system. For example, AVS mechanism 144 may be located anywhere between handpiece 144 and a console unit of the phacoemulsification system, within or coupled with handpiece 140 as exemplified in FIG. 1, along a connection line between the console and handpiece 140, etc. Additionally, in the configuration where AVS mechanism 144 is located in handpiece 140, AVS mechanism 144 may be placed, or coupled to the handpiece, in various locations within the handpiece. For example, AVS mechanism 144 may be coupled with the proximal end of handpiece 140, near the proximal end of handpiece 140, or at distal end 142 thereof.

Generally, operation of the AVS mechanism to cut vacuum operation relates herein to any action that prevents additional vacuum conditions at tip of distal end 142 of handpiece 140. Such actions may include operating one or more valves, generating electrical signal to a pump unit, stop electrical power to the pump or any other respective action. Accordingly, triggering the AVS mechanism relates to operation of the phacoemulsification system for preventing additional vacuum conditions applied to the patient's eye at distal end 142 of the handpiece.

The at least one light source 110 may include one or more laser units and may be configured to emit one or more infrared illumination beams 112 directed to a corneal surface 55 of a patient during an eye operation. The illumination beam 112 is reflected from corneal surface 55 generating one or more reflected beams 114. Detection unit 120 includes one or more detectors, e.g., detectors 120a, 120b, 120c and 120d, and is positioned in path of reflected beams 114 for detecting at least one of intensity location and/or spatial distribution of the reflected beams 114. Detection unit 120 is further connected to a detection circuit 130 configured for collecting and analyzing data on detection of illumination beam 114 from detection unit 120, and to detect variations in at least one of pattern and location of reflected beam 114 impinging on the detectors of detection unit 120. Detection circuit 130 is connected to the phacoemulsification system, and specifically to AVS mechanism 144 thereof, to provide a trigger signal indicative of a variation in surface curvature of cornea 50. The phacoemulsification system is further configured to generate a response signal triggering operation of AVS mechanism 144 when the variation in the reflected beam pattern is indicative of a surface curvature change exceeding a predefined threshold.

Phacoemulsification systems are generally used for eye surgeries such as cataract surgery. In some examples, following an initial incision and after identifying selected regions of the lens, the phacoemulsification system may be operated by the surgeon to emit high frequency vibrations through a needle located at distal end 142 of the handpiece 140, and break up the lens into smaller pieces. The operation further includes aspiration of the emulsified material and irrigation fluid introduced into the eye to maintain the pressure within the eye.

The aspiration operation may cause low pressure conditions within patient's eye, which in turn may cause deformation of the cornea 50 and damage eye. Simultaneous irrigation is generally used to replace the removed material and prevent cornea deformation. Additionally, as indicated above AVS mechanism 144 may be used to stop aspiration, to avoid reduced pressure conditions, e.g., post occlusion surge, within the eye and prevent deformation of the cornea.

Accordingly, the present disclosure utilizes optical inspection of corneal surface 55 to identify variation in surface curvature indicating post occlusion surge and trigger the AVS mechanism in response to the variation in surface curvature. In this connection, according to some examples of the present disclosure, detector unit 120 may be configured with a selected number of detection regions 120a-120d, or as a pixel array having a selected number of pixels. Further, detector unit 120 may be configured to generate output detection data indicative of illumination intensity collected by the different detection regions or pixels. This provides detection of change in location and/or distribution of light collected by detector unit 120. Similarly, illumination beam (s) 112 is reflected from corneal surface 55 of eye and reflected beam(s) 114 is collected by detector unit 120. Accordingly, any change in corneal surface 55 of an eye may result in change in location and/or distribution of reflected beam(s) 114 impinging on the detector unit.

According to some examples, detector unit 120 may operate with a selected sampling rate, for example, the detector unit may generally operate with sampling rate of 1 KHz or more, in some examples at sampling rate of 1.5 KHz or more, and in some examples at rate of 2 KHz or more. Detector unit 120 transmits output detection signals to detection circuit 130, which is configured to collect data on the detection signals from detector unit 120 and determine the level of variation between a previous detection signal and a current detection signal, to thereby determine data on variation in at least one of reflected beam 114 location and spatial distribution. In response to determining variation of reflected beam 114 location and/or spatial distribution that exceeds one or more predetermined thresholds, detection circuit 130 is configured to generate a triggering signal for operating AVS mechanism 144 to cut vacuum operation for aspiration of eye fluid.

Figure 2:
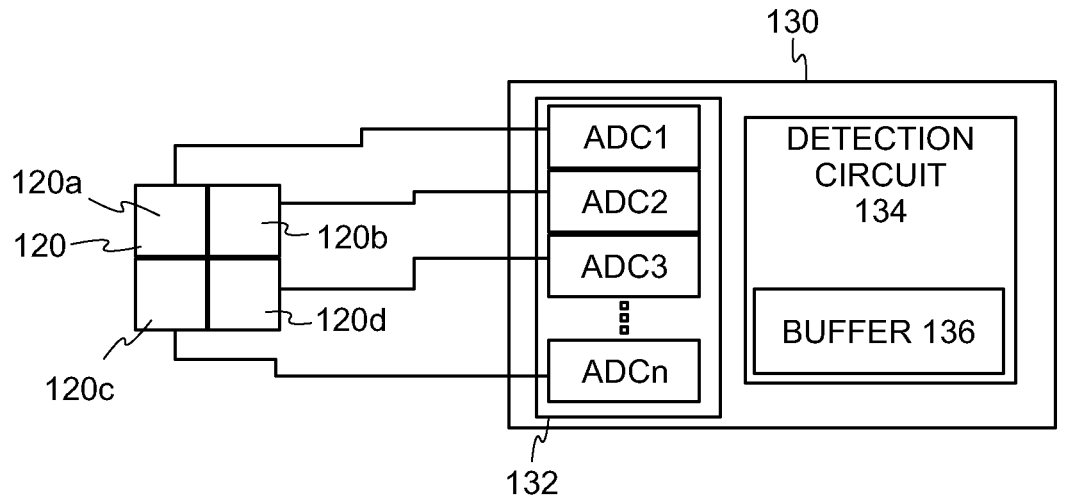
FIG. 2 schematically illustrated a configuration of detector unit and detection circuit according to some examples of the present disclosure.

In some examples of the present disclosure, detection circuit 130 may be an analog circuit configured to minimize processing time. FIG. 2 exemplifies detection circuit 130 and detector unit 120 according to some examples of the present disclosure. As illustrated, detection circuit 130 may include one or more analog to digital conversion circuits 132 including ADC1, ADC2 to ADCn. ADCs 132 are parallelly connected to respective light detectors 120a-120d of detector unit 120 to provide direct communication between the detection regions (pixels) and detection circuit 130. ADC 132 may be configured for obtaining the detection signal from the light detectors and for converting the detection signal to generate digital output data indicative of at least one of spatial location and distribution of illumination beam reflected from the cornea and impinging on the detector unit. In some examples, detector unit 120 may include an arrangement of photodiodes. It should be noted that FIG. 1 exemplifies a number of four light detectors 120a-120d, however, it should be understood that any number of light detectors may be used. Further, in some examples, detector unit 120 may be configured as a pixel array having a number of light detectors may be at least four and may go up to several hundreds or thousands in accordance with the selected detector unit 120.

Detector unit 120 may utilize an arrangement of photodiodes configured such that each photodiode operates as a separate light detector such as light detectors 120a-120d. In some examples, each of light detectors 120a-120d may be formed of a selected number of photodiodes.

ADC 132 is further connected to a decision circuit 134 and/or processor, configured to receive digital output data from ADC 132 and to determine variation in the digital output data between current digital output data and previously received digital output data. Decision circuit 134 may further maintain a buffer 136 for storing digital output data collected within a selected period of e.g., between 2 and 50 sampling instances, enabling monitoring of rate of variation in pattern of collected reflected beam.

In this connection, according to some examples of the present disclosure, decision circuit 134 may operate to determine a level of change in the digital output data between detection instances. If the level of change exceeds a selected threshold, decision circuit 143 may generate a trigger signal to trigger operation of AVS mechanism 144 to cut aspiration operation. In some further examples, decision circuit 134 utilize buffer 136 storage for storing digital output data for a selected period for monitoring variations in pattern of reflected beam 114 associated with changes below the predetermined threshold.

More specifically, according to some examples of the present disclosure, decision circuit 134 may determine change in digital output data between consecutive detection instances. In response to determining that the change in collected signals exceeds a spatial variation threshold, decision circuit 134 operates to generate an AVS trigger signal. Further, in some examples, in response to determining a change in collected signals that is below the spatial variation threshold, decision circuit 134 may utilize buffer 136 to determine rate and duration of a variation in the collected signals. Accordingly, decision circuit 134 may determine is variation of the collected signal throughout a buffering period exceeds a temporal variation threshold, and if the signal variation exceeds the temporal variation threshold, decision circuit 134 operates to generate an AVS trigger signal.

As indicated above, any change in curvature of the corneal surface, on which illumination beam 112 falls, results in respective change in pattern of reflected beam 114 detected by detector unit 120. To provide fast response, the different detectors 120a-120d of detector unit 120 may be connected in parallel to ADCs 132 transmitting output signal to decision circuit 134. Decision circuit 134 determines a level of change in pattern of reflected beam 114 collected by the detector and determines if the change exceeds at least one of spatial threshold indicating fast and large change in reflected beam pattern, and temporal threshold indicating continuous change with relatively slow rate (e.g., change within a few milliseconds). In case decision circuit 134 determines that the variation exceeds one or more of the spatial and temporal thresholds, decision circuit 134 generates an AVS trigger signal to cut aspiration operation.

Further, reference is made to FIG. 3 exemplifying a method for use in eye surgery including providing at least one light source and detector unit in step 3010. According to the present disclosure, the method includes directing one or more illumination beams toward a surface of the cornea of a patient's eye in step 3020, and collecting reflected beam(s) using a detector unit formed of an arrangement of light detectors in step 3030. In some examples, the at least one light source may include at least one laser light source that may be configured to emit one or more illumination beams within the infrared wavelength range. Typically, the illumination beams may be an eye-safe wavelength and intensity. The arrangement of light detectors may include a selected number of four or more light detectors. The light detectors may include one or more photodiodes.

Additionally, in step 3040, the method includes analyzing the reflected beam pattern over time. The analysis may include a comparison between the pattern of the collected beam between consecutive sampling instances, and in some examples may also include comparing the pattern of the collected beam with sampling instances within a selected period. Based on the analysis, the method includes determining if variation in the pattern of collected light is within limits or exceeds one or more predetermined thresholds in step 3050. If the variation in collected patterns exceeds the predetermined threshold, the method includes in step 3060, generating an AVS trigger signal to activate the AVS mechanism for cutting aspiration operation to prevent over exposure of the patient's eye to reduced pressure and avoid collapse of the cornea surface. #

As indicated above, analysis of the detected signal may utilize parallel analog to digital conversion and comparison between collected signal data between detection instances. To provide fast sampling and response, the reflected beam may be detected using high sampling rate, e.g., using sampling rate of 1 KHz or more, or in some examples with sampling rate of 1.5 KHz or more, or using sampling rate of 2 KHz or more. In some examples, the sampling rate and analysis may be sufficient to generate AVS trigger signal within a time frame of up to 3 milliseconds in response to variation in corneal surface curvature.

Reference is further made to FIG. 4 illustrating an additional exemplary method according to the present disclosure. As shown in FIG. 4, the method includes directing one or more illumination beams (e.g., laser illumination beams) toward a surface of a patient's cornea in step 4010. In step 4020 the method includes collecting reflected beam(s) reflected from the corneal surface, using an arrangement of light detectors. The arrangement of light detectors may include an arrangement of photodiodes, or other light detectors having high sampling rate. Further, in step 4030 the method includes generating digital output data for each of the light detectors of the arrangement. The digital output data may be generated in parallel to provide high sampling and processing rates. The method further includes analyzing the digital output data with respect to previously sampled digital output data in step 4040. The analysis includes comparing between the digital output data to determine a variation in pattern of the collected beam impinging on the arrangement of light detectors. If the change between digital output data of consecutive sampling instances exceeds a predetermined spatial threshold, the method includes in step 4050 generating an AVS trigger signal. Additionally, if the change does not exceed the predetermined spatial threshold, the method may include in step 4060, analyzing digital output data with buffer data. More specifically, in some examples, the detection circuit may utilize a buffer for storing digital output data associated with a selected number of sampling instances. This enables determining a pattern of slow variations that do not directly exceed the predetermined spatial threshold, while if such variation proceeds for a prolonged duration (typically a few sampling instances) this may indicate a variation in corneal surface curvature. Accordingly, if the change within a period selected by buffer storage exceeds a predetermined temporal variation threshold, the method further includes in step 4070, generating an AVS trigger signal.

The AVS trigger signal may be transmitted via wired or wireless connection to the AVS mechanism (144 in FIG. 1). In response to the trigger signal, the AVS mechanism operates to cut aspiration operation to avoid placing the patient's eye in under pressure conditions, to thereby avoid damage to the patient's eye.

Accordingly, the present disclosure provides a system and methods for monitoring curvature of a patient's corneal surface and provides for fast triggering of an AVS mechanism in response to detecting variation in corneal curvature. The technique of the present disclosure may utilize fast processing using parallel connection of analog to digital conversion units to enable fast response within a time frame of 3 milliseconds or below.

EXAMPLES

Following is a non-exclusive list of some exemplary examples of the disclosure. The present disclosure also includes examples which include fewer than all the features in an example and examples using features from multiple examples, even if not listed below.

Example 1: A system (100) for use in eye surgery, the system (100) comprising at least one light source (110), a detection unit (120), and a detection circuit (130);

(a) the at least one light source (110) is configured and operable to emit one or more illumination beams (112) directed at a region of a corneal surface of a patient's eye (50);

(b) the detection unit (120) comprising an arrangement of light detectors (120a-120d) positioned for collecting a reflected beam (114) reflected from the region of the corneal surface of the patient's eye (50);

(c) the detection circuit (130) is configured for:

i) collecting a detection signal from the detection unit (120), and ii) analyzing the detection signal to detect variations of the reflected beam (114) pattern over time indicative of surface curvature changes of the corneal surface region, and iii) generating a response signal triggering operation of an anti-vacuum surge (AVS) mechanism (144) when the variation in the reflected beam (114) pattern is indicative of a surface curvature change exceeding a predefined threshold.

Example 2: The system of Example 1, wherein the at least one light source (110) comprises at least one light source operating in an infrared wavelength range.

Example 3: The system of example 1 or 2, wherein the at least one light source (110) is operating in an infrared wavelength range.

Example 4: The system of any one of examples 1 to 3, wherein the detection circuit (130) comprises one or more analog to digital conversion circuits (132) parallelly connected to respective light detectors (120a-120d) of the detection unit (120).

Example 5: The system of any one of example 1 to 4, wherein the variations of the reflected beam (114) pattern comprise variation of at least one of location of the reflected beam impinging on the detector unit (120) and spatial distribution of the reflected beam impinging on the detector unit (120).

Example 6: The system of any one of examples 1 to 5, wherein the detection circuit (130) comprises a decision circuit (134) configured for receiving data indicative of the detection signal from the arrangement of light detectors (120a-120d) and determining data indicative of variations of the reflected beam (114) pattern; the decision circuit (130) being configured to determine a variation level with respect to at least one of a spatial variation threshold and a temporal variation threshold and trigger the AVS mechanism (144) if the variations of the reflected beam (114) pattern exceed at least one of the spatial variation threshold and the temporal variation threshold.

Example 7: The system of any one of examples 1 to 6, wherein the arrangement of light detectors (120a-120d) comprises an arrangement of photodiodes.

Example 8: The system of any one of examples 1 to 7, wherein the detection circuit (130) is configured to generate the response signal to trigger operation of the AVS mechanism (144) within a time frame of up to 3 milliseconds from detection of variations of the reflected light beam (114) pattern indicative of the surface curvature changes of the corneal surface region.

Example 9: The system of any one of examples 1 to 8, wherein the at least one light source (110) is an eye safe laser source.

Example 10: The system of any one of examples 1 to 9, wherein the at least one light source (110) comprises an array of laser light sources.

Example 11: The system of any one of examples 1 to 10, wherein the at least one light source (110) comprises a laser light source and at least one beam splitting arrangement configured to split output beam to form an array of illumination beams (112).

Example 12: A method for use in eye surgery, the method comprising:

directing one or more illumination beams toward a surface of a cornea of a patient's eye (3020), detecting a reflected beam by an arrangement of light detectors (3030), determining a reflected beam pattern over a period of time (3040), comparing the reflected beam pattern over time to at least one of a spatial threshold or a temporal threshold (3050), and in response to the reflected beam pattern over time exceeding the spatial threshold or the temporal threshold, generating an anti-vacuum surge (AVS) mechanism trigger signal (3060) to eliminate or at least significantly reduce damage due to a collapse of the cornea.

Example 13: The method of example 12, wherein the reflected beam pattern comprises at least one of location of reflected beam impinging on the arrangement of light detectors (120a-120d), and distribution of illumination of the reflected beam impinging on the arrangement of light detectors (120a-120d).

Example 14: The method of example 12 or 13, wherein the arrangement of light detectors (120a-120d) comprises an arrangement of photodiodes.

Example 15: The method of example 14, further comprising operating a detection circuit (130) comprising one or more analog to digital conversion circuits (132) respectively connected to one or more photodiodes of the arrangement of light detectors, to generate high-speed output data on the reflected beam pattern.

Example 16: The method of example 15, wherein the output data on the reflected beam pattern comprises data on least one of location and spatial distribution of the reflected beam.

Example 17: The method of example 15 or 16, wherein operating the one or more analog to digital conversion circuits (132) comprises operating the analog to digital conversion circuits (132) in parallel.

Example 18: The method of any one of examples 11 to 17, configured for operating the AVS mechanism within a time frame of up to 3 milliseconds from detection of the reflected beam by the arrangement of light detectors (120a-120d).

Example 19: The method of any one of examples 11 to 18, wherein the directing one or more illumination beams comprises operating at least one laser source for illuminating the cornea surface of a patient's eye.

Example 20: The method of any one of examples 11 to 19, wherein the directing one or more illumination beams (112) comprises directing one or more infrared illumination beams (112) characterizes by optical wavelength range that is invisible to the human eye.

Example 21: The method of any one of examples 11 to 20, wherein the directing one or more illumination beams (112) comprises operating at least one laser source (110), wherein the at least one laser source (110) is configured to emit an infrared illumination beam.

Example 22: The method of any one of examples 11 to 21, wherein the directing one or more illumination beams (112) comprises operating at least one eye safe laser source.

Those skilled in the art to which the present disclosure pertains, can appreciate that while the present disclosure has been described in terms of preferred examples, the concept upon which this disclosure is based may readily be utilized as a basis for the designing of other structures, systems, and processes for carrying out the several purposes of the present disclosure.

Also, it is to be understood that the phraseology and terminology employed herein are for the purpose of description and should not be regarded as limiting. It should be noted that the words "comprising", "including" and "having" as used throughout the appended claims are to be interpreted to mean "including but not limited to". The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases, and disjunctively present in other cases. The term "each" may not be exclusively understood as referring to each and every, and when technically relevant may also refer to "at least some".

All patents and patent applications mentioned in this specification are herein incorporated in their entirety by reference into the specification, to the same extent as if each individual patent or patent application was specifically and individually indicated to be incorporated herein by reference. In addition, citation, or identification of any reference in this application shall not be construed as an admission that such reference is available as prior art to the present disclosure.

It is important, therefore, that the scope of the present disclosure is not construed as being limited by the illustrative examples set forth herein. Other variations are possible within the scope of the present disclosure as defined in the appended claims. Other combinations and sub-combinations of features, functions, elements and/or properties may be claimed through amendment of the present claims or presentation of new claims in this or a related application. Such amended or new claims, whether they are directed to different combinations or directed to the same combinations, whether different, broader, narrower or equal in scope to the original claims, are also regarded as included within the subject matter of the present description.

The invention claimed is:

1. A system for use in eye surgery, the system comprising at least one light source, a detection unit, and a detection circuit;

(a) the at least one light source is configured and operable to emit one or more illumination beams directed at a region of a corneal surface of a patient's eye;

(b) the detection unit comprising an arrangement of light detectors positioned for collecting a reflected beam reflected from the region of the corneal surface of the patient's eye;

(c) the detection circuit is configured for:

i) collecting a detection signal from the detection unit, and ii) analyzing the detection signal to detect variations of the reflected beam pattern over time indicative of surface curvature changes of the corneal surface region, and iii) generating a response signal triggering operation of an anti-vacuum surge (AVS) mechanism when the variation in the reflected beam pattern is indicative of a surface curvature change exceeding a predefined threshold.

2. The system of claim 1, wherein the at least one light source comprises at least one light source operating in an infrared wavelength range.

3. The system of claim 1, wherein the detection circuit comprises one or more analog to digital conversion circuits parallelly connected to respective light detector of the detection unit.

4. The system of claim 1, wherein the variations of the reflected beam pattern comprise variation of at least one of location of the reflected beam impinging on the detector unit and spatial distribution of the reflected beam impinging on the detector unit.

5. The system of claim 1, wherein the detection circuit comprises a decision circuit configured for receiving data indicative of the detection signal from the arrangement of light detectors and determining data indicative of variations of the reflected beam pattern; the decision circuit being configured to determine a variation level with respect to at least one of a spatial variation threshold and a temporal variation threshold and trigger the AVS mechanism if the variations of the reflected beam pattern exceed at least one of the spatial variation threshold and the temporal variation threshold.

6. The system of claim 1, wherein the arrangement of light detectors comprises an arrangement of photodiodes.

7. The system of claim 1, wherein the detection circuit is configured to generate the response signal to trigger operation of the AVS mechanism within a time frame of up to 3 milliseconds from detection of variations of the reflected light beam pattern indicative of the surface curvature changes of the corneal surface region.

8. The system of claim 1, wherein the at least one light source is an eye safe laser source.

9. The system of claim 1, wherein the at least one light source comprises an array of laser light sources.

10. The system of claim 1, wherein the at least one light source comprises a laser light source and at least one beam splitting arrangement configured to split output beam to form an array of illumination beams.

* * * * *